(12) United States Patent
Forde et al.

(10) Patent No.: US 7,658,747 B2
(45) Date of Patent: Feb. 9, 2010

(54) MEDICAL DEVICE FOR MANIPULATION OF A MEDICAL IMPLANT

(75) Inventors: Sean Forde, Watertown, MA (US); Carol A. Ryan, Topsfield, MA (US)

(73) Assignee: NMT Medical, Inc., Boston, MA (US)

( * ) Notice: Subject to any disclaimer, the term of this patent is extended or adjusted under 35 U.S.C. 154(b) by 493 days.

(21) Appl. No.: 10/386,828

(22) Filed: Mar. 12, 2003

(65) Prior Publication Data
US 2004/0181237 A1 Sep. 16, 2004

(51) Int. Cl.
*A61M 29/00* (2006.01)
*A61F 2/06* (2006.01)

(52) U.S. Cl. .................. 606/200; 623/1.11

(58) Field of Classification Search ........... 623/1.11, 623/1.12, 1.13; 606/200, 106, 108, 127, 606/110, 113, 114, 1, 194; 128/898
See application file for complete search history.

(56) References Cited

U.S. PATENT DOCUMENTS

| | | | | |
|---|---|---|---|---|
| 3,050,066 A | * | 8/1962 | Koehn | 604/97.01 |
| 3,502,069 A | * | 3/1970 | Silverman | 600/587 |
| 3,800,781 A | * | 4/1974 | Zalucki | 600/562 |
| 3,874,388 A | | 4/1975 | King et al. | 128/334 R |
| 3,875,648 A | | 4/1975 | Bone | |
| 3,924,631 A | | 12/1975 | Mancusi | |
| 4,006,747 A | | 2/1977 | Kronenthal et al. | |
| 4,007,743 A | | 2/1977 | Blake | 128/334 R |
| 4,425,908 A | | 1/1984 | Simon | |
| 4,606,347 A | * | 8/1986 | Fogarty et al. | 606/194 |
| 4,650,466 A | * | 3/1987 | Luther | 604/95.04 |
| 4,696,300 A | | 9/1987 | Anderson | |
| 4,710,192 A | | 12/1987 | Liotta et al. | |
| 4,836,204 A | | 6/1989 | Landymore et al. | 128/334 R |
| 4,902,508 A | | 2/1990 | Badylak et al. | |
| 4,915,107 A | | 4/1990 | Rebuffat et al. | |
| 4,921,484 A | * | 5/1990 | Hillstead | 604/104 |
| 4,946,440 A | | 8/1990 | Hall | |
| 4,956,178 A | | 9/1990 | Badylak et al. | |
| 4,985,014 A | | 1/1991 | Orejola | 600/16 |
| 5,021,059 A | | 6/1991 | Kensey et al. | |
| 5,030,199 A | | 7/1991 | Barwick et al. | 600/29 |
| 5,037,433 A | | 8/1991 | Wilk et al. | |

(Continued)

FOREIGN PATENT DOCUMENTS

EP 1013227 12/1999

(Continued)

OTHER PUBLICATIONS

International Search Report for PCT/US2004/007288 dated Nov. 26, 2004.

(Continued)

*Primary Examiner*—Anhtuan T Nguyen
*Assistant Examiner*—Elizabeth Houston

(57) ABSTRACT

This invention relates to medical devices for manipulating medical implants such as, for example, stents, distal protection filters, and septal occluders in a patient's body, and the methods of use thereof. Generally, a medical device of the invention includes a sleeve and an expandable component joined to the sleeve which transitions between a collapsed configuration and a deployed configuration for capturing a medical implant in a patient's body.

9 Claims, 11 Drawing Sheets

U.S. PATENT DOCUMENTS

| | | | |
|---|---|---|---|
| 5,041,090 A | 8/1991 | Scheglov et al. | |
| 5,041,129 A | 8/1991 | Hayhurst et al. | 606/232 |
| 5,042,976 A | 8/1991 | Ishitsu et al. | 604/96 |
| 5,057,114 A | 10/1991 | Wittich et al. | 606/127 |
| 5,073,166 A | 12/1991 | Parks et al. | 609/93 |
| 5,100,429 A | 3/1992 | Sinofsky et al. | |
| 5,108,420 A | 4/1992 | Marks | 606/213 |
| 5,112,310 A | 5/1992 | Grobe | 604/175 |
| 5,171,259 A | 12/1992 | Inoue | |
| 5,176,687 A * | 1/1993 | Hasson et al. | 606/114 |
| 5,190,528 A | 3/1993 | Fonger et al. | 604/171 |
| 5,192,301 A | 3/1993 | Kamiya et al. | 606/213 |
| 5,222,974 A | 6/1993 | Kensey et al. | |
| 5,236,440 A | 8/1993 | Hlavacek | |
| 5,257,637 A | 11/1993 | El Gazayerli | |
| 5,275,826 A | 1/1994 | Badylak et al. | |
| 5,282,827 A | 2/1994 | Kensey et al. | |
| 5,284,488 A | 2/1994 | Sideris | 606/213 |
| 5,304,184 A | 4/1994 | Hathaway et al. | |
| 5,312,341 A | 5/1994 | Turi | 604/96 |
| 5,312,417 A * | 5/1994 | Wilk | 606/114 |
| 5,312,435 A | 5/1994 | Nash et al. | |
| 5,330,446 A | 7/1994 | Weldon et al. | |
| 5,334,217 A | 8/1994 | Das | |
| 5,354,308 A | 10/1994 | Simon et al. | |
| 5,357,979 A | 10/1994 | Imran | 128/772 |
| 5,370,647 A * | 12/1994 | Graber et al. | 606/127 |
| 5,370,661 A | 12/1994 | Branch | 606/232 |
| 5,383,899 A | 1/1995 | Hammerslag | |
| 5,385,156 A | 1/1995 | Oliva | |
| 5,403,338 A | 4/1995 | Milo | 606/184 |
| 5,411,481 A | 5/1995 | Allen et al. | |
| 5,413,584 A | 5/1995 | Schulze | |
| 5,417,699 A | 5/1995 | Klein et al. | |
| 5,425,744 A | 6/1995 | Fagan et al. | 606/213 |
| 5,433,727 A | 7/1995 | Sideris | 606/213 |
| 5,451,235 A | 9/1995 | Lock et al. | 606/213 |
| 5,480,424 A | 1/1996 | Cox | |
| 5,486,193 A | 1/1996 | Bourne et al. | |
| 5,507,811 A | 4/1996 | Koike et al. | 623/11 |
| 5,540,712 A | 7/1996 | Kleshinski et al. | 606/198 |
| 5,545,138 A | 8/1996 | Fugoso et al. | 604/102 |
| 5,571,135 A * | 11/1996 | Fraser et al. | 623/1.12 |
| 5,573,542 A | 11/1996 | Stevens | |
| 5,577,299 A | 11/1996 | Thompson et al. | 24/131 C |
| 5,578,045 A | 11/1996 | Das | 606/151 |
| 5,601,571 A | 2/1997 | Moss | |
| 5,618,311 A | 4/1997 | Gryskiewicz | |
| 5,620,461 A | 4/1997 | Muijs Van De Moer et al. | |
| 5,626,599 A | 5/1997 | Bourne et al. | |
| 5,634,936 A | 6/1997 | Linden et al. | 606/213 |
| 5,649,950 A | 7/1997 | Bourne et al. | |
| 5,653,684 A | 8/1997 | Laptewicz | 604/22 |
| 5,662,703 A * | 9/1997 | Yurek et al. | 623/1.12 |
| 5,681,324 A * | 10/1997 | Kammerer et al. | 606/113 |
| 5,683,411 A | 11/1997 | Kavteladze et al. | 606/200 |
| 5,693,085 A | 12/1997 | Buirge et al. | |
| 5,702,421 A | 12/1997 | Schneidt | 606/213 |
| 5,709,707 A | 1/1998 | Lock et al. | 606/213 |
| 5,720,754 A | 2/1998 | Middleman et al. | 606/127 |
| 5,725,552 A | 3/1998 | Kotula et al. | 606/213 |
| 5,733,294 A | 3/1998 | Forber et al. | 606/151 |
| 5,733,337 A | 3/1998 | Carr, Jr. et al. | |
| 5,741,297 A | 4/1998 | Simon | 606/213 |
| 5,746,765 A | 5/1998 | Kleshinksi et al. | 606/198 |
| 5,776,162 A | 7/1998 | Kleshinski | 606/198 |
| 5,797,960 A | 8/1998 | Stevens et al. | |
| 5,800,516 A | 9/1998 | Fine et al. | |
| 5,807,384 A | 9/1998 | Mueller | |
| 5,810,884 A | 9/1998 | Kim | |
| 5,823,956 A | 10/1998 | Roth et al. | |
| 5,829,447 A | 11/1998 | Stevens et al. | |
| 5,853,422 A | 12/1998 | Huebsch et al. | |
| 5,855,614 A | 1/1999 | Stevens et al. | |
| 5,861,003 A | 1/1999 | Latson et al. | |
| 5,865,791 A | 2/1999 | Whayne et al. | |
| 5,868,753 A | 2/1999 | Schatz | 606/108 |
| 5,879,366 A | 3/1999 | Shaw et al. | 606/213 |
| 5,893,856 A | 4/1999 | Jacob et al. | |
| 5,895,404 A | 4/1999 | Ruiz | 606/185 |
| 5,902,317 A | 5/1999 | Kleshinski et al. | 606/198 |
| 5,902,319 A | 5/1999 | Daley | |
| 5,904,703 A | 5/1999 | Gilson | 606/213 |
| 5,919,200 A | 7/1999 | Stambaugh et al. | 606/159 |
| 5,924,424 A | 7/1999 | Stevens et al. | |
| 5,928,250 A | 7/1999 | Koike et al. | |
| 5,944,738 A | 8/1999 | Amplatz et al. | 606/213 |
| 5,948,427 A | 9/1999 | Yamamoto et al. | |
| 5,955,110 A | 9/1999 | Patel et al. | |
| 5,976,172 A | 11/1999 | Homsma et al. | 606/200 |
| 5,976,174 A | 11/1999 | Ruiz | 606/213 |
| 5,989,268 A | 11/1999 | Pugsley, Jr. et al. | |
| 5,993,475 A | 11/1999 | Lin et al. | |
| 5,993,844 A | 11/1999 | Abraham et al. | |
| 5,997,556 A | 12/1999 | Tanner | 606/153 |
| 5,997,575 A | 12/1999 | Whitson et al. | |
| 6,007,558 A | 12/1999 | Ravenscroft et al. | 606/200 |
| 6,010,517 A | 1/2000 | Baccaro | |
| 6,024,756 A | 2/2000 | Huebsch et al. | 606/213 |
| 6,030,007 A | 2/2000 | Bassily et al. | 289/1.5 |
| 6,030,405 A | 2/2000 | Zarbatany et al. | 606/191 |
| 6,039,721 A * | 3/2000 | Johnson et al. | 604/508 |
| 6,056,760 A | 5/2000 | Koike et al. | 606/148 |
| 6,066,158 A | 5/2000 | Engelson et al. | 606/200 |
| 6,077,291 A | 6/2000 | Das | |
| 6,079,414 A | 6/2000 | Roth | |
| 6,080,182 A | 6/2000 | Shaw et al. | 606/213 |
| 6,086,610 A | 7/2000 | Duerig et al. | 623/1 |
| 6,096,053 A | 8/2000 | Bates | 606/159 |
| 6,096,347 A | 8/2000 | Geddes et al. | |
| 6,106,532 A | 8/2000 | Koike et al. | 606/138 |
| 6,106,913 A | 8/2000 | Scardino et al. | |
| 6,113,609 A | 9/2000 | Adams | |
| 6,117,159 A | 9/2000 | Huebsch et al. | 606/213 |
| 6,126,686 A | 10/2000 | Badylak et al. | |
| 6,129,755 A | 10/2000 | Mathis et al. | 623/1.15 |
| 6,132,438 A | 10/2000 | Fleischman et al. | |
| 6,143,037 A | 11/2000 | Goldstein et al. | |
| 6,149,664 A | 11/2000 | Kurz | 606/194 |
| 6,152,144 A | 11/2000 | Lesh et al. | |
| 6,156,055 A * | 12/2000 | Ravenscroft | 606/206 |
| 6,165,183 A | 12/2000 | Kuehn et al. | |
| 6,165,204 A | 12/2000 | Levinson et al. | |
| 6,168,579 B1 | 1/2001 | Tsugita | 604/96.01 |
| 6,171,329 B1 | 1/2001 | Shaw et al. | 606/213 |
| 6,174,322 B1 | 1/2001 | Schneidt | 606/213 |
| 6,179,859 B1 | 1/2001 | Bates et al. | 606/200 |
| 6,187,016 B1 * | 2/2001 | Hedges et al. | 606/108 |
| 6,187,039 B1 | 2/2001 | Hiles et al. | |
| 6,190,353 B1 | 2/2001 | Makower et al. | |
| 6,200,313 B1 | 3/2001 | Abe et al. | |
| 6,203,559 B1 | 3/2001 | Davis et al. | 606/198 |
| 6,206,895 B1 | 3/2001 | Levinson | |
| 6,206,907 B1 | 3/2001 | Marino et al. | 606/215 |
| 6,213,976 B1 | 4/2001 | Trerotola | 604/104 |
| 6,214,029 B1 | 4/2001 | Thill et al. | 606/213 |
| 6,216,696 B1 | 4/2001 | Van den Berg | 128/207.14 |
| 6,217,590 B1 | 4/2001 | Levinson | |
| 6,221,006 B1 | 4/2001 | Dubrul et al. | 600/159 |
| 6,221,092 B1 | 4/2001 | Koike et al. | 606/213 |
| 6,228,097 B1 | 5/2001 | Levinson et al. | |
| 6,231,561 B1 | 5/2001 | Frazier et al. | |
| 6,245,080 B1 | 6/2001 | Levinson | |
| 6,258,026 B1 | 7/2001 | Ravenscroft et al. | 600/200 |

| | | |
|---|---|---|
| 6,265,333 B1 | 7/2001 | Dzenis et al. |
| 6,270,515 B1 | 8/2001 | Linden et al. |
| 6,277,138 B1 | 8/2001 | Levinson et al. |
| 6,287,317 B1 | 9/2001 | Makower et al. |
| 6,290,674 B1 | 9/2001 | Roue et al. .................. 604/107 |
| 6,299,635 B1 | 10/2001 | Frantzen |
| 6,306,150 B1 | 10/2001 | Levinson |
| 6,306,424 B1 | 10/2001 | Vyakarnam et al. |
| 6,312,446 B1 | 11/2001 | Huebsch et al. ............. 606/213 |
| 6,315,791 B1 | 11/2001 | Gingras et al. |
| 6,319,263 B1 | 11/2001 | Levinson |
| 6,322,548 B1 | 11/2001 | Payne et al. .................. 604/500 |
| 6,328,727 B1 | 12/2001 | Frazier et al. |
| 6,334,872 B1 | 1/2002 | Termin et al. |
| 6,342,064 B1 | 1/2002 | Koike et al. ................. 606/213 |
| 6,344,049 B1 | 2/2002 | Levinson et al. |
| 6,346,074 B1 | 2/2002 | Roth .......................... 600/121 |
| 6,348,041 B1 | 2/2002 | Klint |
| 6,352,531 B1 | 3/2002 | O'Connor et al. ............. 606/15 |
| 6,352,552 B1 | 3/2002 | Levinson et al. |
| 6,355,052 B1 | 3/2002 | Neuss et al. ................. 606/213 |
| 6,364,853 B1 | 4/2002 | French et al. |
| 6,369,039 B1 | 4/2002 | Palasis et al. |
| 6,371,971 B1 | 4/2002 | Tsugita et al. .............. 606/200 |
| 6,375,625 B1 | 4/2002 | French et al. |
| 6,375,671 B1 | 4/2002 | Kobayashi et al. .......... 606/213 |
| 6,379,342 B1 | 4/2002 | Levinson |
| 6,379,368 B1 | 4/2002 | Corcoran et al. ............ 606/153 |
| 6,387,104 B1 | 5/2002 | Pugsley, Jr. et al. |
| 6,391,048 B1 | 5/2002 | Ginn et al. |
| 6,398,796 B2 | 6/2002 | Levinson |
| 6,402,772 B1 | 6/2002 | Amplatz et al. |
| 6,419,669 B1 | 7/2002 | Frazier et al. |
| 6,436,088 B2 | 8/2002 | Frazier et al. |
| 6,440,152 B1 | 8/2002 | Gainor et al. ............... 606/213 |
| 6,460,749 B1 | 10/2002 | Levinson et al. |
| 6,482,210 B1 | 11/2002 | Skiba et al. ................... 606/86 |
| 6,482,224 B1 | 11/2002 | Michler et al. |
| 6,488,706 B1 | 12/2002 | Solymar |
| 6,494,888 B1 | 12/2002 | Laufer et al. |
| 6,517,550 B1 * | 2/2003 | Konya et al. ................. 606/113 |
| 6,537,198 B1 | 3/2003 | Vidlund et al. ................ 600/16 |
| 6,551,303 B1 | 4/2003 | Van Tassel et al. |
| 6,551,344 B2 | 4/2003 | Thill |
| 6,569,181 B1 * | 5/2003 | Burns ......................... 606/198 |
| 6,596,013 B2 | 7/2003 | Yang et al. |
| 6,608,040 B1 | 8/2003 | Lin et al. |
| 6,623,508 B2 | 9/2003 | Shaw et al. |
| 6,623,518 B2 | 9/2003 | Thompson et al. ......... 623/1.11 |
| 6,666,861 B1 | 12/2003 | Grabek |
| 6,712,836 B1 | 3/2004 | Berg et al. |
| 6,726,696 B1 | 4/2004 | Houser et al. |
| 6,866,679 B2 * | 3/2005 | Kusleika .................... 623/1.11 |
| 6,939,348 B2 | 9/2005 | Malecki et al. |
| 7,165,552 B2 | 1/2007 | Deem et al. |
| 2001/0014800 A1 | 3/2001 | Burg et al. |
| 2001/0034537 A1 | 10/2001 | Shaw et al. |
| 2001/0037129 A1 | 11/2001 | Thill ......................... 606/213 |
| 2001/0039435 A1 | 11/2001 | Roue et al. |
| 2001/0041914 A1 | 11/2001 | Roue et al. |
| 2001/0041915 A1 | 11/2001 | Frazier et al. |
| 2001/0044639 A1 | 11/2001 | Levinson |
| 2001/0049492 A1 | 12/2001 | Frazier et al. |
| 2002/0010481 A1 | 1/2002 | Jayaraman |
| 2002/0129819 A1 | 1/2002 | Feldman et al. |
| 2002/0019648 A1 | 2/2002 | Akerfeldt et al. |
| 2002/0026208 A1 | 2/2002 | Roe et al. |
| 2002/0029048 A1 | 3/2002 | Miller |
| 2002/0032462 A1 | 3/2002 | Houser et al. |
| 2002/0035374 A1 | 3/2002 | Borillo et al. |
| 2002/0043307 A1 | 4/2002 | Ishida et al. |
| 2002/0052572 A1 | 5/2002 | Franco et al. |
| 2002/0055767 A1 * | 5/2002 | Forde et al. ................ 623/1.11 |
| 2002/0077555 A1 | 6/2002 | Schwartz |
| 2002/0084178 A1 | 7/2002 | Dubson et al. |
| 2002/0096183 A1 | 7/2002 | Stevens et al. |
| 2002/0099389 A1 | 7/2002 | Michler et al. ............... 606/139 |
| 2002/0107531 A1 | 8/2002 | Schreck et al. |
| 2002/0111637 A1 | 8/2002 | Kaplan et al. |
| 2002/0120323 A1 | 8/2002 | Thompson et al. ......... 623/1.11 |
| 2002/0128680 A1 | 9/2002 | Pavlovic ..................... 606/200 |
| 2002/0161427 A1 * | 10/2002 | Rabkin et al. .............. 623/1.11 |
| 2002/0169377 A1 | 11/2002 | Khairkhahan et al. |
| 2002/0183786 A1 | 12/2002 | Girton ........................ 606/213 |
| 2002/0183787 A1 | 12/2002 | Wahr et al. .................. 606/213 |
| 2002/0183823 A1 | 12/2002 | Pappu |
| 2003/0028213 A1 | 2/2003 | Thill et al. |
| 2003/0045893 A1 | 3/2003 | Ginn .......................... 606/151 |
| 2003/0050665 A1 | 3/2003 | Ginn .......................... 606/215 |
| 2003/0059640 A1 | 3/2003 | Marton et al. |
| 2003/0065379 A1 | 4/2003 | Babbs et al. |
| 2003/0073979 A1 | 4/2003 | Naimark et al. |
| 2003/0100920 A1 | 5/2003 | Akin et al. |
| 2003/0114879 A1 * | 6/2003 | Euteneuer et al. ........... 606/200 |
| 2003/0139819 A1 | 7/2003 | Beer et al. |
| 2003/0191495 A1 | 10/2003 | Ryan et al. |
| 2003/0191526 A1 | 10/2003 | Van Tassel et al. |
| 2003/0195530 A1 | 10/2003 | Thill |
| 2003/0204203 A1 | 10/2003 | Khairkhahan et al. |
| 2003/0208232 A1 | 11/2003 | Blaeser et al. .............. 606/213 |
| 2004/0044361 A1 | 3/2004 | Frazier et al. |
| 2004/0073230 A1 * | 4/2004 | Mulholland et al. ......... 606/108 |
| 2004/0143291 A1 | 7/2004 | Corcoran et al. |
| 2004/0181237 A1 | 9/2004 | Forde et al. |
| 2004/0210301 A1 | 10/2004 | Obermiller |
| 2004/0230185 A1 | 11/2004 | Malecki et al. |
| 2004/0243122 A1 | 12/2004 | Auth et al. |
| 2004/0267191 A1 | 12/2004 | Gifford, III et al. |
| 2005/0021016 A1 | 1/2005 | Malecki et al. |
| 2005/0080406 A1 | 4/2005 | Malecki et al. |
| 2005/0131401 A1 | 6/2005 | Malecki et al. |
| 2005/0131460 A1 | 6/2005 | Gifford, III et al. |
| 2006/0027241 A1 | 2/2006 | Malecki et al. |
| 2006/0074410 A1 | 4/2006 | Malecki et al. |
| 2006/0241581 A1 | 10/2006 | Malecki et al. |
| 2006/0241582 A1 | 10/2006 | Malecki et al. |
| 2006/0241583 A1 | 10/2006 | Malecki et al. |
| 2006/0241584 A1 | 10/2006 | Malecki et al. |
| 2006/0247612 A1 | 11/2006 | Malecki et al. |
| 2006/0271030 A1 | 11/2006 | Francis et al. |
| 2006/0271040 A1 | 11/2006 | Horne et al. |
| 2006/0271089 A1 | 11/2006 | Alejandro et al. |
| 2006/0276779 A1 | 12/2006 | Malecki et al. |
| 2006/0276846 A1 | 12/2006 | Malecki et al. |
| 2007/0010806 A1 | 1/2007 | Malecki et al. |

FOREIGN PATENT DOCUMENTS

| | | |
|---|---|---|
| EP | 1 046 375 A1 | 10/2000 |
| EP | 1 222 897 A2 | 7/2002 |
| IE | WO 00/44428 * | 3/2000 |
| WO | 94/25099 | 11/1994 |
| WO | WO 96/25179 | 8/1996 |
| WO | WO 96/31157 | 10/1996 |
| WO | WO 98/07375 | 2/1998 |
| WO | WO 98/26738 | 6/1998 |
| WO | WO 99/05977 | 2/1999 |
| WO | WO 99/18862 | 4/1999 |
| WO | WO 99/18864 | 4/1999 |
| WO | WO 99/18870 | 4/1999 |
| WO | WO 99/18871 | 4/1999 |
| WO | WO 99/30640 | 6/1999 |
| WO | WO 00/27292 | 5/2000 |
| WO | WO 01/08600 | 2/2001 |
| WO | WO 01/21247 | 3/2001 |
| WO | WO 01/26702 | 4/2001 |

| WO | WO 01/30266 | 5/2001 |
| WO | WO 01/30267 | 5/2001 |
| WO | WO 01/30268 | 5/2001 |
| WO | WO 01/49185 | 7/2001 |
| WO | WO 01/78596 | 10/2001 |
| WO | WO 01/93783 | 12/2001 |
| WO | WO 02/17809 | 3/2002 |
| WO | WO 02/24106 | 3/2002 |
| WO | WO 03/022159 | 3/2003 |
| WO | WO 03/059152 | 7/2003 |
| WO | WO 03/061481 | 7/2003 |
| WO | WO 03/073944 | 9/2003 |
| WO | WO 03/077733 A2 | 9/2003 |

OTHER PUBLICATIONS

"Elastic Deployment," SMST-2000 Proceedings of the International Conference on Shape Memory and Superelastic Technologies, Apr. 30 to May 4, 2000, Asilomar Conference Center, 3 pages.

"Trans-septal Catheterization for Radiofrequency Catheter Ablation of Cardiac Arrhythmias. Results and Safety of a Simplified Method," by R. De Ponti, et al., European Heart Journal, vol. 19, Jun. 1998, pp. 943-950.

"The Puncture Needle as Guidewire: Needle Guide Technique for Percutaneous Nephrostomy," by Irvin F. Hawkins, Jr., M.D., et al., Seminars in Interventional Radiology, vol. 4, No. 2, Jun. 1987, pp. 126-130.

"PFO and Stroke: The Hidden Connection," by Paul Kramer, MD, Endovascular Today, http://www.endovasculartoday.com/02_current/10.html, printed Oct. 9, 2003.

"The Puncture Technique: A New Method of Transcatheter Closure of Patent Foramen Ovale," by Carlos E. Ruiz, M.D., Ph.D., et al., Catheterization and Cardiovascular Interventions, vol. 53, 2001, pp. 369-372.

"New Transseptal Puncture Technique for Transcatheter Closure of Patent Foramen Ovale," by Robert J. Sommer, M.D., et al., Mount Sinai Medical Center, New York, New York, publication date unknown, but believed to be Jun. 2002 or earlier.

"Microvena—Uniquely Innovative Interventional Products," Microvena press release from http://www.microvena.com/MVC-NEWS.html, printed on Jan. 27, 2003.

James Hansen, "Metals that Remember," Science 81, June, pp. 44-47.

Morris Simon and Aubrey M. Palestrant "Transvenous Devices for the Management of Pulmonary Embolism", Cardiovascular and Interventional Radiology by Springer-Verlag 1980, 308-318, 1980.

Morris Simon, M.D., Roy Kaplow, Ph.D., Edwin Salzman, M.D., and David Freiman, M.D., A Vena Cava Filter Using Thermal Shape Memory Alloy, Radiology, vol. 125, No. 1, Oct. 1977, pp. 89-94.

International Preliminary Examination Report for PCT/US2004/007288, mailed Sep. 29, 2005.

Kimura et al., "Effects of Neutron Irradiation on the Transformation Behavior in Ti-Ni Alloys," Abstract, Proceedings of the Int'l Conf. on Mariensitic Transformations (1992) 935-940.

National Aeronautics and Space Administration, "55-Nitinol-the Alloy with a Memory: Its Physical Mettallurgy, Properties, and Applications," A-Report, 24-25.

Patent Cooperation Treaty (PCT) International Search Report (PCT Article 18 and Rules 43 and 44), International Application No. PCT/US2004/019919, International Filing Date: Nov. 22, 2004, Applicant: NMT Medical, Inc.

Patent Cooperation Treaty (PCT) Written Opinion of the International Searching Authority (PCT Rule 43bis.1), International Application No. PCT/US2004/019919, International Filing Date: Nov. 22, 2004, Applicant: NMT Medical, Inc.

Ramanathan et al., "Experimental and Computational Methods for Shape Memory Alloys," 15th ASCE Engineering Mechanics Conf. (Jun. 2-5, 2002) 12 pages.

Shabalovskaya, "Surface, Corrosion and Biocompatibility Aspects of Nitinol as an Implant Material," Bio-Medical Materials and Engineering, (2002) 12:69-109.

Stöckel, "Nitinol Medical Devices and Implants," *SMST-2000: Proceedings of the International Conference on Shape Memory and Suerelastic Technologies*, 531-540.

Uchil, "Shape Memory Alloys-Characterization Techniques," Pramana-Journal of Physics, (2002) 58(5-6):1131-1139.

* cited by examiner

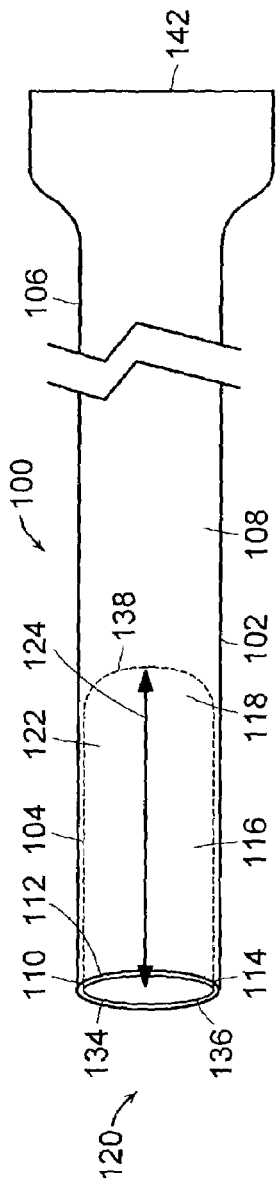
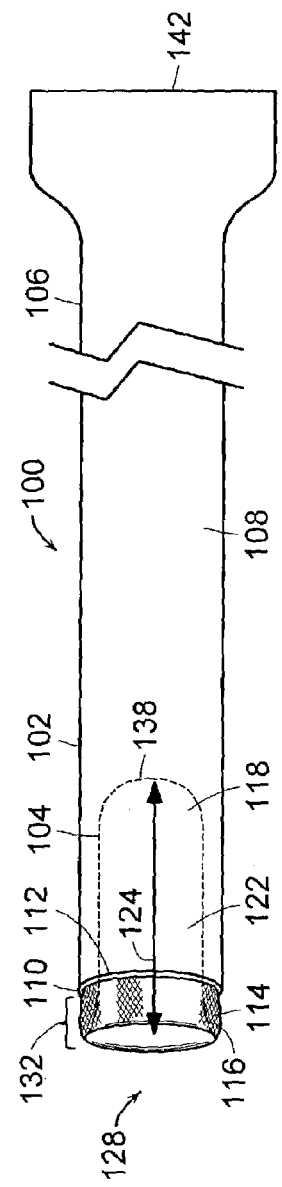
FIG. 1A
FIG. 1B

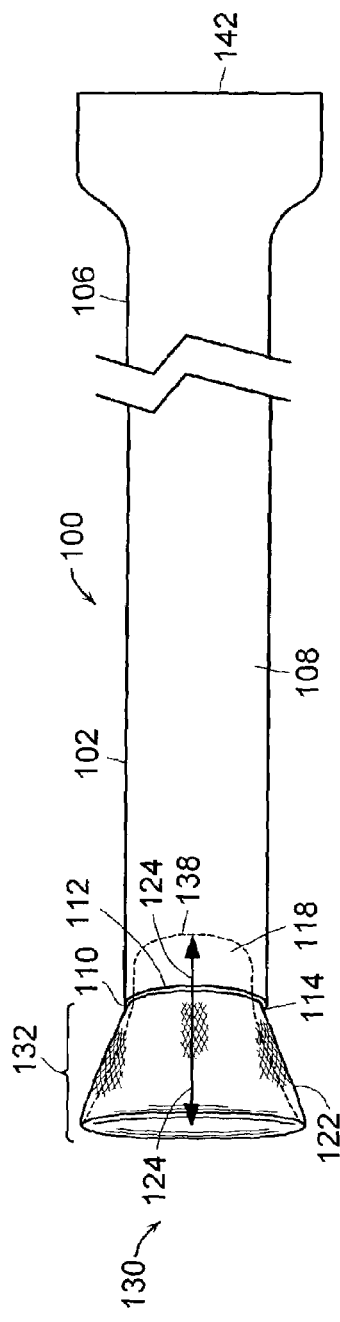
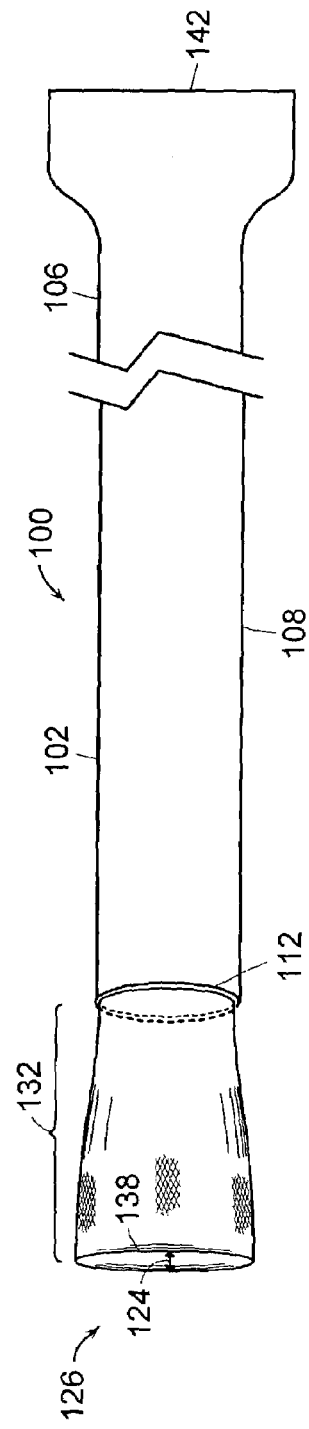

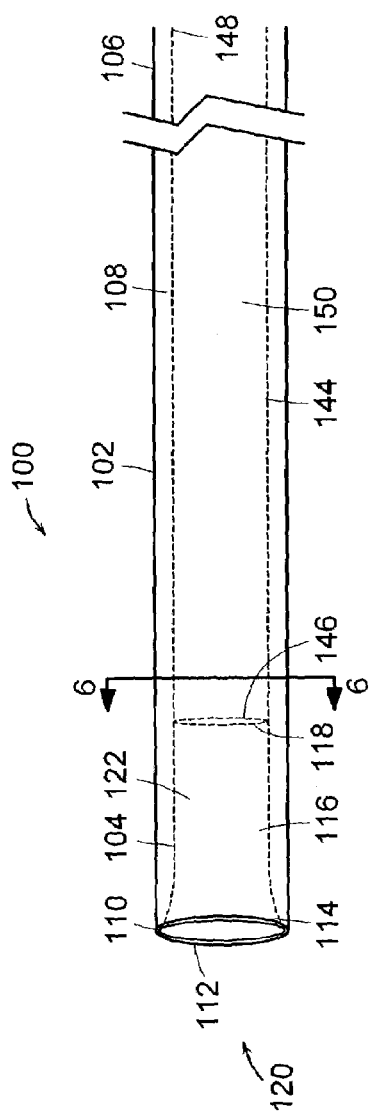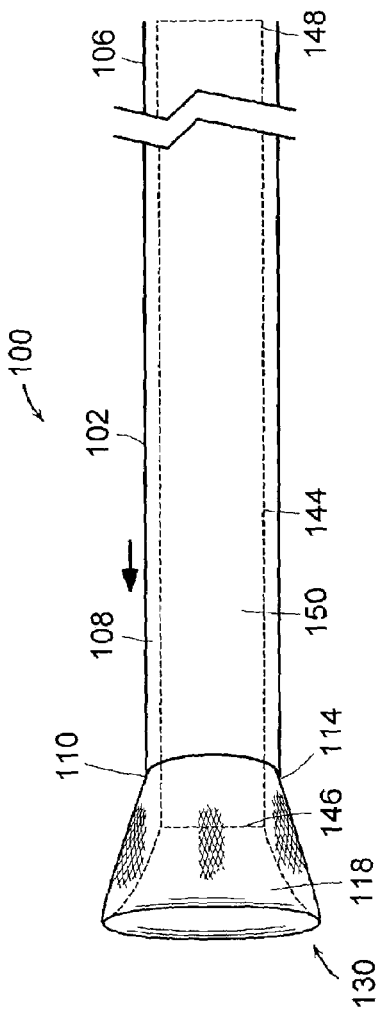

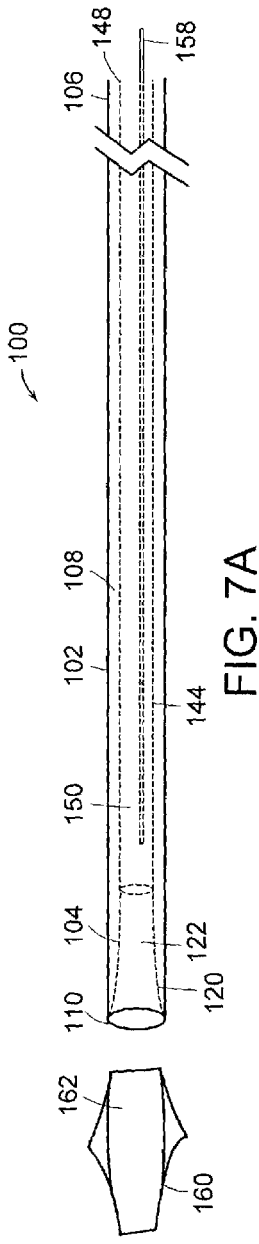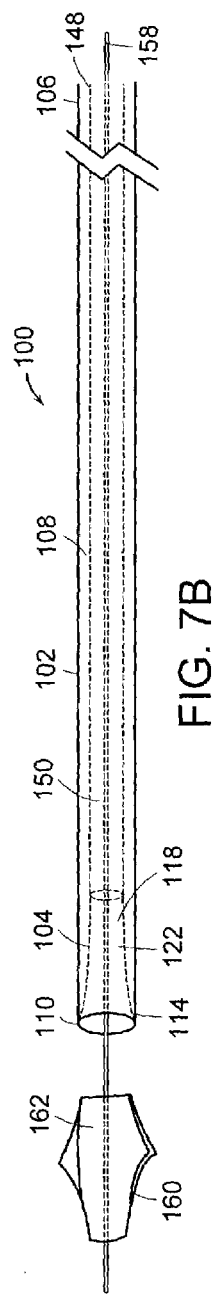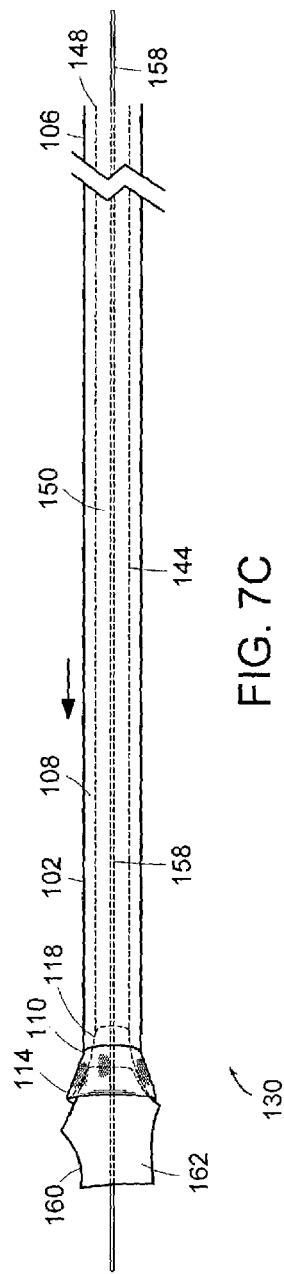

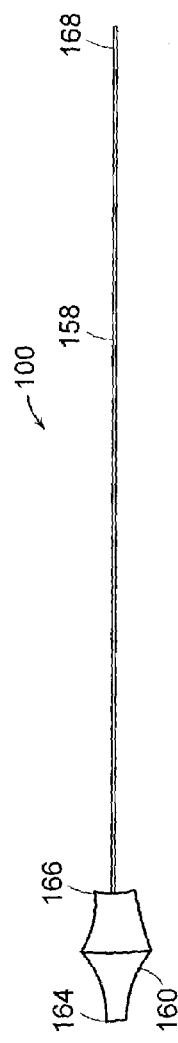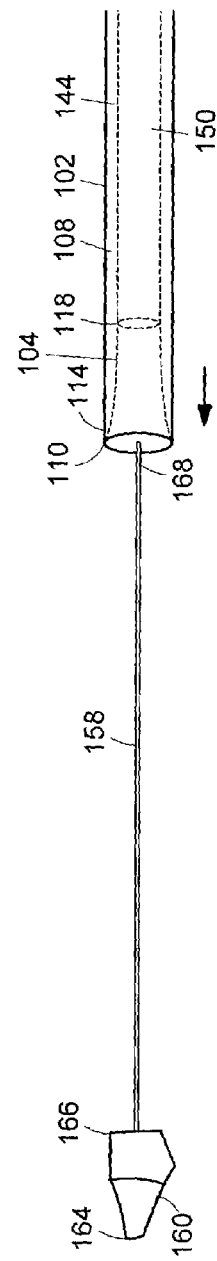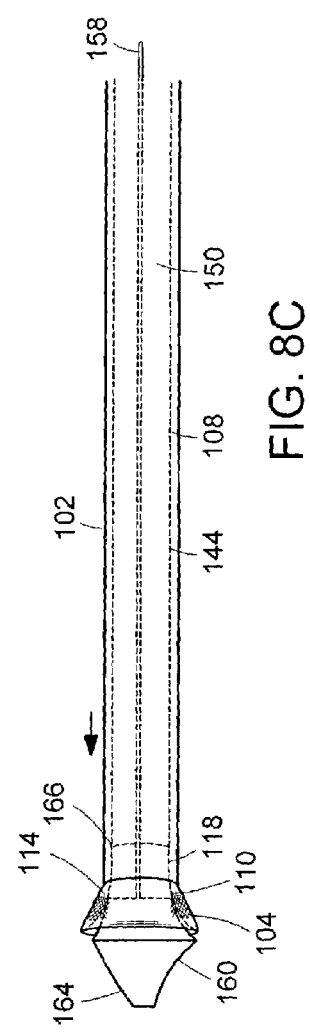

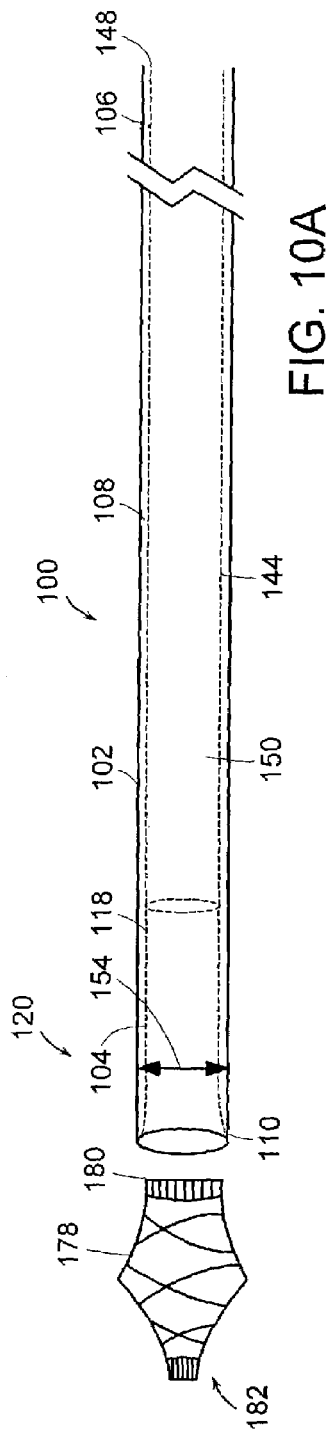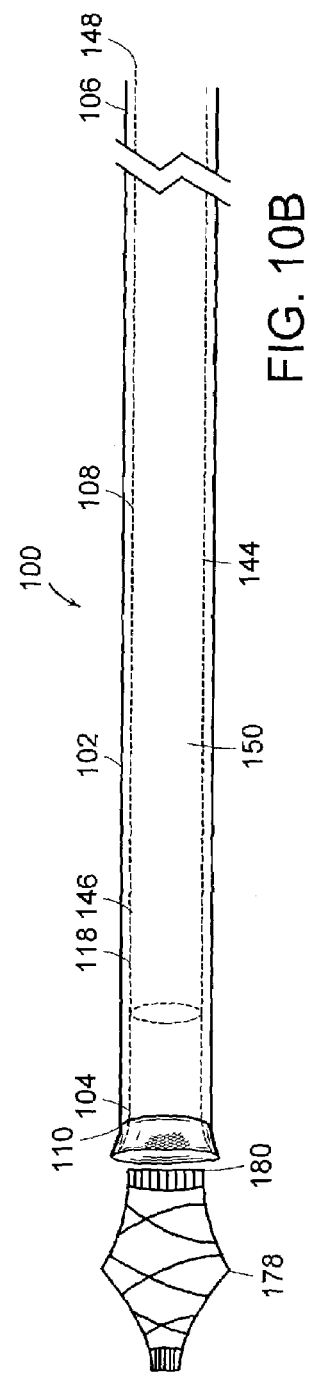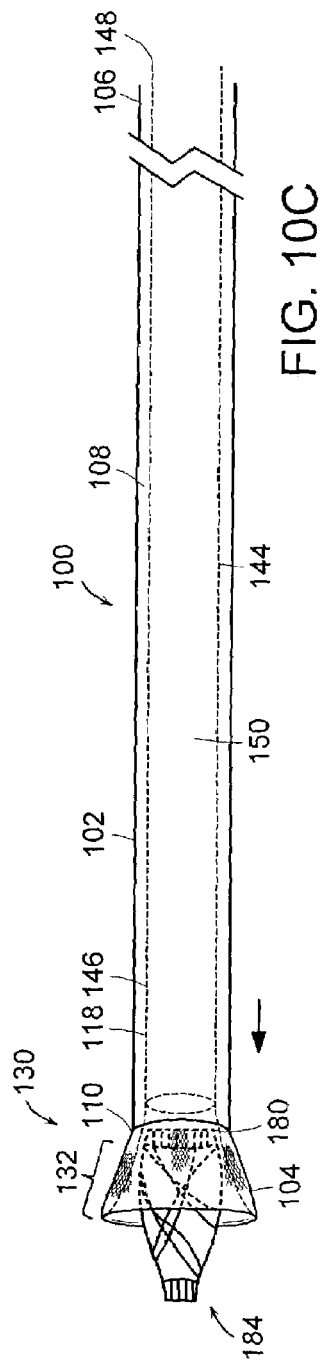

MEDICAL DEVICE FOR MANIPULATION OF A MEDICAL IMPLANT

FIELD OF THE INVENTION

This invention generally relates to a cardiovascular medical device. More particularly, this invention relates to a medical device for manipulating a medical implant in the cardiovascular system of a patient and methods of use of such a medical device.

BACKGROUND OF THE INVENTION

Medical implants have wide-spread use in percutaneous vascular and cardiac surgery. These implants include, in particular, distal protection filter devices for the capture of thrombi in major veins such as the lower caval vein, occlusion devices for permanent or temporary obturation of a vessel lumen or permanent occlusion of defects in cardiac walls such as an atrial septal defect (ASD), a patent ductus arteriosus (PDA), or other cardiovascular defects such as, patent foramen ovale (PFO) and left atrial appendage (LAA).

Cardiac wall septal defects are usually congenital in nature leading to abnormal openings, holes or shunts between the chambers of the heart or the great blood vessels, causing abnormal shunting of blood through the opening. Such defects may result, for example, from the incomplete formation of the septum, or wall, between cardiac chambers during fetal life when the heart develops from a folded tube into a four chambered, two unit system. These deformities can result in significant health risks such as, high pulmonary arterial pressures and fatal heart failure, if not corrected.

Initially, atrial septal defects were corrected by open heart surgery. However, in order to avoid the morbidity and mortality associated with open heart surgery, a variety of transcatheter closure techniques have been attempted in patients. In such techniques, a medical implant such as an occluding device, is delivered percutaneously through an intravascular catheter into a patient. Once the occluding device is positioned adjacent the defect, it is attached to the wall adjacent the septum in a manner which permits it to effectively block the passage of blood through the defect. One such medical implant is a septal occluder which is inserted percutaneously via a catheter into a chamber of the heart to occlude a septal defect in a patient. A septal occluder is typically adapted very closely to the shape and size of the defect which is to be closed and is positioned very precisely upon implantation into the patient's heart. However, in the event that the septal occluder is dislodged from its intended location, or misaligned with the defect, it is often difficult to retrieve the septal occluder due to its shape or size. Furthermore, the process of retrieving the septal occluder often causes damage to the surrounding vasculature.

In addition to the use of medical implants for the treatment of septal defects, medical implants are also used to capture embolic debris caused by medical procedures that blood vessels stenosed or occluded in a patient caused by the deposit of plaque or other material on the walls of the blood vessels. Angioplasty, for example, is a widely known medical procedure wherein a dilating device, such as an inflatable balloon, is introduced into the occluded region of the vessel. The balloon is inflated, dilating the occlusion and thereby increasing intraluminal diameter. Plaque material may be inadvertently dislodged during angioplasty. This material is free to travel downstream, possibly lodging within another portion of the blood vessel that may supply a vital organ thereby causing damage to the organ by obstructing blood flow to the organ.

Medical implants such as distal protection filters are typically introduced into the desired blood vessel for capturing embolic debris dislodged during angioplasty. One of the problems associated with the removal of a medical implant such as a distal protection filter from a patient's body is that the retrieval process results in the collapse of the distal protection filter causing egress of particulate embolic matter back into the bloodstream. In the case of cerebral angioplasty, for example, emboli dislodged during the retrieval of a distal protection filter from a patient's body may travel to the brain, possibly causing a stroke, which can lead to permanent neurological injuries or even the death of the patient. Therefore, while distal protection filters are useful for trapping embolic debris that is dislodged or generated during a medical procedure, such as angioplasty, the egress of embolic debris trapped in a distal protection filter back into the bloodstream of a patient while the distal protection filter is being removed from the patient's body remains a problem.

SUMMARY OF THE INVENTION

The invention disclosed herein relates to medical devices and the methods of use of the medical devices for manipulating medical implants in patients. The medical devices of the invention result in a significant reduction in or prevention of problems and risks associated with the recovery or delivery of medical implants in patients such as, for example, escape of embolic debris from a distal protection filter as it is being removed from a patient or damaging of blood vessels during the delivery or retrieval of a septal occluder from a patient.

A medical device according to the invention can be used to capture a medical implant for retrieval or delivery into a patient's body.

In one aspect, the invention is directed to a medical device including a sleeve and an expandable component. The sleeve includes a lumen, a distal end and a proximal end and at least a portion of the expandable component is joined to the sleeve. The expandable component transitions between a collapsed state when the expandable component is enclosed by the sleeve, and a deployed state when a portion of the expandable component is extended beyond the distal end of the sleeve. The expandable component is sized and shaped for manipulating a medical implant in a patient's body. For example, in one embodiment, manipulating includes capturing a medical implant for recovery from or delivering of the medical implant inside a patient's body.

In one embodiment, the medical device of the invention further includes an elongate member. The elongate member includes a distal end and a proximal end and at least a portion of the elongate member is slideably moveable within the lumen of the sleeve. In one embodiment, at least a portion of the expandable component is joined to the elongate member. In a particular embodiment, at least a portion of the expandable component is joined to the distal end of the elongate member.

In various embodiments of the foregoing aspect of the invention, the expandable component of the medical device is joined to the distal end of the sleeve.

The expandable component is deployed by relative sliding motion of the sleeve and the expandable component. In one embodiment, the expandable component is reciprocatably moveable relative to the sleeve, wherein the sleeve is stationary. In another embodiment, the sleeve is reciprocatably moveable relative to the expandable component, wherein the expandable component is stationary. The expandable component may also be deployed by relative sliding motion of the elongate member within the lumen of the sleeve relative to the sleeve.

In one embodiment, the expandable component has a conical shape in the deployed state. The expandable component may be sized and shaped to manipulate a septal occluder. The expandable component may also be sized and shaped to manipulate a distal protection filter.

In another aspect, the invention relates to methods for manipulating a medical implant in a patient's body using the aforementioned medical devices of the invention. One method of the invention includes providing a medical device of the invention including a sleeve with a lumen, a distal end and a proximal end and an expandable component, where at least a portion of the distal portion of the expandable component is joined to the sleeve and the expandable component transitions between a collapsed state when the expandable component is enclosed by the sleeve and a deployed state when a portion of the expandable component is extended beyond the distal end of the sleeve, the expandable component being sized and shaped for manipulating a medical implant in a patient's body.

Another method of the invention includes providing the medical device that further includes an elongate member that is slideably moveable within the lumen of the sleeve.

In one embodiment, manipulating a medical implant using a method according to the invention includes capturing a medical implant for delivery inside a patient's body using the medical device of the invention. In another embodiment, manipulating a medical implant using the method according to the invention includes capturing a medical implant for retrieval from a patient's body.

In other aspects, the invention relates to a medical device for capturing a medical implant in a patient's body including a sleeve means, an expandable means, and means for deploying the expandable means beyond the sleeve means. At least a portion of the expandable means is joined to the sleeve means and the expandable means transitions between a collapsed state when the expandable means is enclosed by the sleeve means and a deployed state when a portion of the expandable means is extended beyond the sleeve means, the expandable means being sized and shaped for capturing the medical implant in the patient's body.

In all embodiments of the foregoing aspects of the invention, the medical implant to be captured can be a septal occluder, a stent or a distal protection filter.

In all the foregoing aspects of the invention, the expandable component can be fabricated from several materials and can assume many configurations. Suitable materials include any material that is flexible, collapsible and atraumatic. In one embodiment, the expandable component includes a mesh that is cylindrical. In another embodiment, the expandable component includes braided material. The expandable component can assume many configurations such as a braid or an elastomeric tube. The braid configuration can include multiple braids or a partial braid.

The directional terms distal and proximal require a point of reference. The term "distal" refers to a direction that points away from an operator of a medical device in accordance with the invention and into the patient's body. The term "proximal" refers to a direction that points toward an operator of the medical device in accordance with the invention and away from the patient's body.

These and other objects, along with advantages and features of the present invention herein disclosed, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to corresponding parts throughout the different views. The drawings are not necessarily to scale, emphasis instead being placed on illuminating the principles and concepts of the invention.

FIG. 1A illustrates a partially-sectioned schematic view of an embodiment of a medical device in accordance with the invention including the expandable component in a collapsed configuration;

FIG. 1B illustrates a partially-sectioned schematic view of an embodiment of the medical device illustrated in FIG. 1A including the expandable component in a partially-deployed configuration;

FIG. 1C illustrates a partially-sectioned schematic view of an embodiment of the medical device illustrated in FIG. 1A including the expandable component in a substantially-deployed configuration;

FIG. 1D illustrates a partially-sectioned schematic view of an embodiment of the medical device illustrated in FIG. 1A including the expandable component in a fully-deployed configuration;

FIG. 4A illustrates a partially-sectioned schematic view of an embodiment of a medical device in accordance with the invention including a lumen extending substantially through the entire length of the elongate member of the medical device;

FIG. 4B illustrates a partially-sectioned schematic view of an embodiment of the medical device illustrated in FIG. 4A including the expandable component in a substantially-deployed configuration for capturing a medical implant;

FIG. 7A illustrates a partially-sectioned schematic view of an embodiment of the medical device illustrated in FIG. 5A including a guide wire and a medical implant with a lumen;

FIG. 7B illustrates a partially-sectioned schematic view of the medical device illustrated in FIG. 7A, where the guide wire is extended substantially through the entire length of the medical device and the medical implant and beyond the distal end of the medical implant;

FIG. 7C illustrates a partially-sectioned schematic view of the medical device illustrated in FIG. 7A including the expandable component capturing the medical implant;

FIG. 8A illustrates a schematic view of a medical implant including a guide wire attached to a medical implant;

FIG. 8B illustrates a partially-sectioned schematic view of an embodiment of the medical device illustrated in FIG. 8A, where the distal end of the sleeve of the medical device is adjacent the free end of the guide wire;

FIG. 8C illustrates a partially-sectioned schematic view of an embodiment of the medical device illustrated in FIG. 8A including the expandable component of the medical device capturing the medical implant;

FIG. 10A illustrates a partially-sectioned schematic view of an embodiment of the medical device illustrated in FIG. 5A in accordance with the invention, including the expandable component in a collapsed configuration and the distal end of the sleeve aligned with a collapsible medical implant;

FIG. 10B illustrates a partially-sectioned schematic view of the medical device of FIG. 10A including the expandable component in a partially-deployed configuration adjacent the proximal portion of the collapsible medical implant; and FIG. 10C illustrates a partially-sectioned schematic view of the medical device of FIG. 10A including the expandable component in a substantially-deployed configuration capturing the medical implant in a substantially-collapsed state.

DESCRIPTION

Figure 2A:
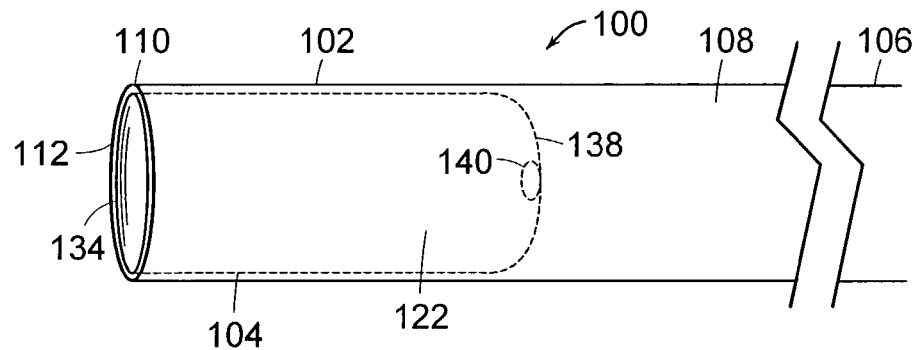
FIG. 2A illustrates a partially-sectioned schematic view of an embodiment of a medical device in accordance with the invention including an expandable component with an open proximal section.

Embodiments of the present invention are described below. The invention is not limited to these embodiments, and various modifications to the disclosed embodiments are also encompassed by the invention. A medical device according to the invention can be used to manipulate a medical implant in a patient's body. In one embodiment, the medical device is used for capturing a medical implant in a patient such as, for example, a vascular distal protection filter or a cardiac septal occluder.

Referring to FIG. 1A, a medical device 100 according to the invention includes a sleeve 102, an expandable component 104, and an actuator 142. The sleeve 102 includes a proximal end 106, and a lumen 108 that extends longitudinally within at least a portion of the sleeve 102 and terminates at a distal end 110 of the sleeve 102. The distal end 110 of the sleeve 102 has a circumference 112. The expandable component 104 includes a first portion 114, a second portion 116 and a third portion 118. The first portion 114 of the expandable component 104 is permanently joined around the circumference of the distal end 110 of the sleeve 102 and includes a lumen 122. The third portion 118 of the expandable component 104 is the portion that is closest to the proximal end 106 of the sleeve 102 when the expandable component 104 is in a collapsed state 120, as illustrated in FIG. 1A. The intermediate or second portion 116 of the expandable component 104 extends between the first portion 114 and the third portion 118 and includes the lumen 122 that extends between the first portion 114 of the expandable component 104 and the third portion 118 of the expandable component 104. The lumen 122 of the expandable component 104 includes a depth 124.

In one embodiment according to the invention, the expandable component 104 is slideably moveable in the lumen 108 of the sleeve 102 transitioning between the collapsed configuration 120 through substantially deployed states illustrated in FIGS. 1B and 1C, to a fully-deployed configuration 126, illustrated in FIG. 1D. In one embodiment, the actuator 142 reciprocatably slides the expandable component 104 between the collapsed configuration 120 and the fully-deployed configuration 126, and any configuration between the collapsed configuration 120 and the fully-deployed configuration 126, depending on the intended application of the medical device 100. Alternatively, the actuator 142 may actuate the sleeve 102 reciprocatably while the expandable component 104 is stationary.

Referring to FIG. 1A, in the collapsed configuration 120, the expandable component 104 is enclosed within the lumen 108 of the sleeve 102. The expandable component 104 in the collapsed configuration 120 includes a lumen 122 with a depth indicated by arrow 124. The depth 124 of the lumen 122 of the expandable component 104 decreases as the expandable component transitions from the collapsed configuration 120, illustrated in FIG. 1A, to the fully-deployed configuration 126, illustrated in FIG. 1D. In the fully-deployed state 126, the depth 124 is almost nil or close to zero.

The configuration of the expandable component 104 when it transitions between the collapsed configuration 120 and the expanded configuration 126 is determined by the intended application of the medical device 100 in a patient's body. For example, for application of the medical device for capturing a medical implant, referring to FIGS. 1B and 1C, the expandable component 104 is configured between the collapsed configuration 120 and the fully-deployed configuration 126. As the expandable component 104 is deployed, the third portion 118 of the expandable component 104 moves toward the distal end 110 of the sleeve 102, pushing the second portion 116 of the expandable component 104, which lies proximal to the first portion 114 when the expandable component 104 is in the collapsed configuration 120, beyond the distal end 110 of the sleeve 102. For example, referring to FIG. 1B, in an intermediate or partially-deployed configuration 128 of the expandable component 104, the third portion 118 of the expandable component 104 moves in a proximal direction toward the distal end 110 of the sleeve 102, resulting in at least a portion of the second portion 116 of the expandable component 104 extruded beyond the distal end 110 of the sleeve 102. Referring now to FIG. 1C, a substantially-deployed configuration 130 of the expandable component 104 is illustrated. In this embodiment, the length of the extruded portion 132 of the expandable component 104 is greater than the length of the expandable component 104 that remains enclosed within the lumen 108 of the sleeve 102. Referring to FIG. 1D, which depicts a fully-deployed configuration 126 of the expandable component 104, the entire length of the expandable component 104 is extruded beyond the distal end of the sleeve 102. The length of the extruded portion 132 of the expandable element 104 in the fully-deployed state 126 is the full length of the expandable element 104 within the lumen 108 of the sleeve 102 in the collapsed configuration 120. The length of the extruded portion 132 of the expandable component 104 beyond the distal end 110 of the sleeve 102 is selected according to the intended application of the medical device 100 in the patient's body. 100531 Referring again to FIGS. 1A-1D, the length of the extruded portion 132 varies from none in the collapsed configuration 120, illustrated in FIG. 1A, to increasing magnitude in the various deployed states illustrated in FIGS. 1B-1D, with the length of the extruded portion 132 being maximal in the fully-deployed configuration 126, illustrated in FIG. 1D. For example, in one embodiment, the extruded portion 132 formed by the expandable component 104 is shaped and sized for capturing a medical implant such as a prosthetic occluder in a patient's body. Accordingly, the configuration of the expandable component 104 lies between the collapsed configuration 120 and the fully-deployed configuration 126.

With continued reference to FIGS. 1A-1D, in one embodiment, the expandable component 104 has a pocket with a depth 124. The first portion 114 of the expandable component 104 is open and has a rim 134 with a circumference 136. The third portion 118 of the expandable component 104 is closed and has a base 138 forming the bottom of the pocket. The rim 134 of the expandable component 104 is joined to the distal end 110 of the sleeve 102 at a plurality of points about the circumference 136 of the rim 134. For example, the rim 134 of the expandable component 104 may be joined to the distal end 110 of the sleeve 102 by an adhesive, sutures, crimping, or heat welding, for example. In one embodiment according to the invention, the circumference 136 of the rim 134 of the expandable component 104 is joined to the circumference 112 of the distal end 110 of the sleeve 102.

Figure 2B:
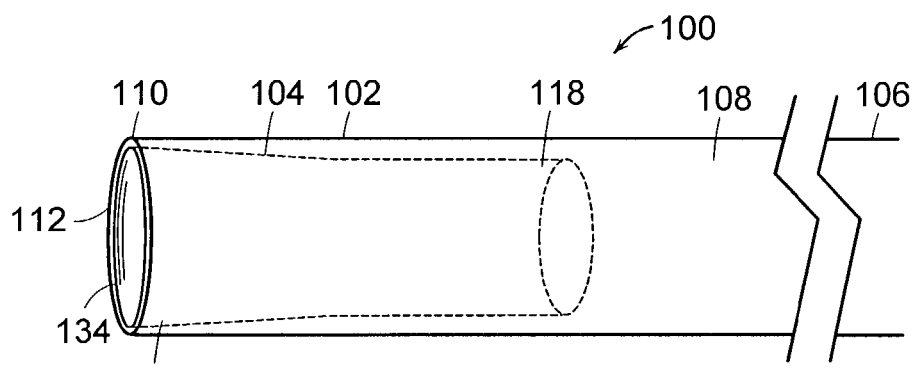
FIG. 2B illustrates a partially-sectioned schematic view of an embodiment of a medical device in accordance with the invention including a cylindrical expandable component with open distal and proximal portions.
Figure 2C:
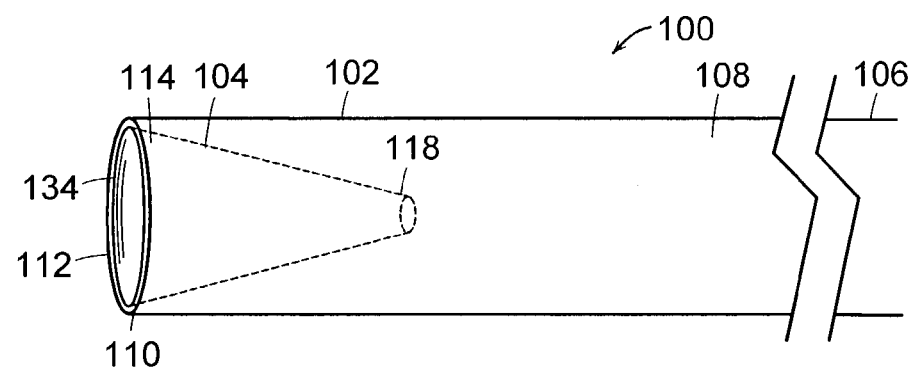
FIG. 2C illustrates a partially-sectioned schematic view of an embodiment of a medical device in accordance with the invention including a funnel-shaped expandable component.

In another embodiment according to the invention, referring now to FIG. 2A, the expandable component 104 may be a tube. The base 138 of the tubular expandable component 104 may be imperforate or perforate. For example, illustrated in FIG. 2A, the base 138 may surround a hole 140. The hole 140 may be useful for axially slideable movement of, for example, a guide wire in the lumen 108 of the sleeve 102 and through the lumen 122 of the expandable component 104. In a particular embodiment, illustrated in FIG. 2B, the expandable component 104 is tubular having a cylindrical shape with an open first portion 114 and an open third portion 118. In yet another embodiment, illustrated in FIG. 2C, the expandable component 104 is funnel shaped having an open first portion 114 and an open or third portion 118.

In all the foregoing aspects of the invention, the overall length of the medical device 100 is selected according to the intended application of the medical device 100 in the patient's body. The overall length of the medical device 100 depends on the specific blood vessel in the patient's body in which the medical implant is located. Generally, the overall length will be in the range of about 25 cm to about 175 cm. In one embodiment, the overall length of the medical device 100 is about 100 cm to about 150 cm, and preferably about 120 cm. Devices for different applications, or those intended for use with children, will be of different lengths.

The expandable component 104 of the medical device 100 may be made from a variety of materials that are flexible and largely atraumatic. Examples of such materials include, for example, polyester, nylon, and steel. In one embodiment, the expandable component 104 is a tube that is made from a braided material. The braided material can be manufactured in part or entirely from a plastic, a fabric, or a metal or any combinations of the above. In one embodiment, the braided material is made of a combination of polyester and steel. In a preferred embodiment, the steel is incorporated into the polyester. Generally, the ratio of steel to polyester in the braided material ranges from about 0.2 to about 0.5 and preferably about 0.25. The braided material can either be single-stranded or multi-stranded. The braided material can be formed as a mesh of individual filaments of materials such as, for example, polyester, polyethylene terephthalate or PET, polypropylene, nitinol, steel or any combinations of these materials. In a particular embodiment, the braided material is inverted over itself and secured to the distal end 110 of the sleeve 102. In another embodiment, the expandable component 104 is a woven or elastomeric tube or sock. Suitable materials for the manufacture of the expandable component 104 in the form of an elastomeric tube include at least in part, for example, PEBAX (ATOFINA Chemicals, Inc., Philadelphia, Pa.), KRATON (Kraton Polymers, Houston, Tex.), C-Flex (silicone modified thermoplastic elastomers) (Consolidated Polymer Technologies, Largo, Fla.), polyurethane, expandable polytetrafluoroethylene or PTFE or any combinations of these materials. In yet another embodiment, the expandable component 104 is a cylindrical mesh. In a preferred embodiment, the expandable component 104, in any configuration, includes a lubricious coating. Suitable materials for the manufacture of the lubricious coating include at least in part, for example, TEFLON (Dupont, Wilmington, Del.), a hydrophilic coating, polyethylene oxide, hydrogel or any combinations of these materials.

The maximum outer diameter of the expandable component 104 in the deployed configuration is dependent on its intended application inside a patient's body. The maximum outer diameter of the expandable component 104 in the deployed configuration must be no greater than the inside diameter of the blood vessel into which the medical device 100 is inserted. For example, to capture an intravascular distal protection filter, the outer diameter of the expandable component 104 in a substantially-deployed configuration 130 typically is in the range of about 4 mm to about 8 mm, preferably about 6 mm, whereas to capture an interatrial septal occluder, the outer diameter of the expandable component 104 in a substantially-deployed configuration 130 typically is in the range of about 17 mm to about 43 mm, preferably about 25 mm.

Similarly, the entire length of the expandable component 104 and accordingly, the length 132 of the expandable component 104 extruded beyond the distal end 110 of the sleeve 102 depends on the application of the medical device 100. For example, the length of the extruded portion 132 in the fully-deployed configuration, which is equal to the full length of the expandable element 104, typically is in the range of about 10 mm to about 30 mm, preferably about 25 mm when the medical implant intended to be captured is an intravascular distal protection filter, whereas the length of the extruded portion 132 in the fully-deployed configuration typically is in the range of about 25 mm to about 100 mm, preferably about 90 mm when the medical implant intended to be captured is an interatrial septal occluder.

Figure 3A:
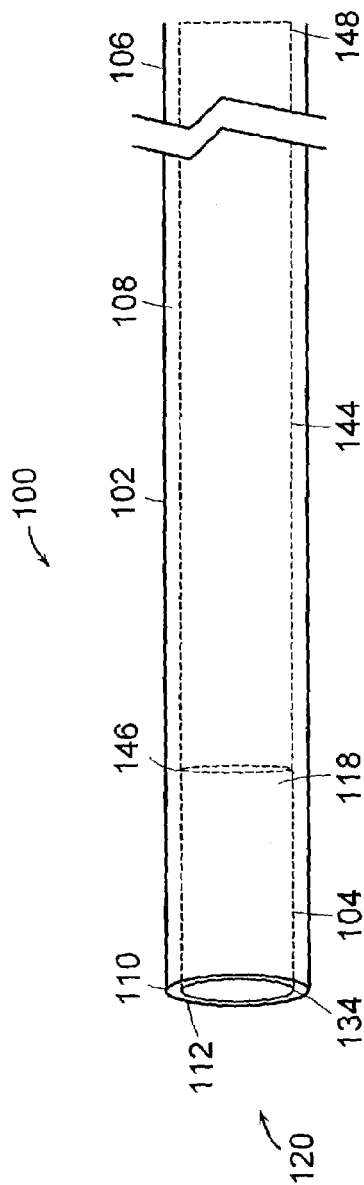
FIG. 3A illustrates a partially-sectioned schematic view of an embodiment of a medical device in accordance with the invention including an elongate member.
Figure 3B:
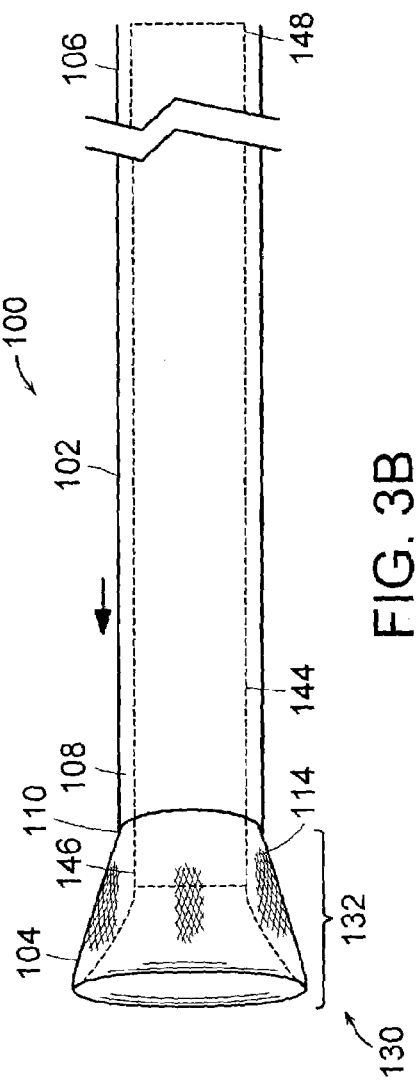
FIG. 3B illustrates s a partially-sectioned schematic view of an embodiment of the medical device illustrated in FIG. 3A including the expandable component in a substantially-deployed configuration for capturing a medical implant.

Referring now to FIGS. 3A and 3B, in one embodiment according to the invention, the medical device 100 includes an elongate member 144 axially positioned and slideably moveable within the lumen 108 of the sleeve 102. The elongate member 144 includes a distal end 146 and a proximal end 148. In one embodiment, referring to FIG. 4A, the third portion 118 of the expandable component 104 is secured to the distal end 148 of the elongate member 144 and the rim 134 of the expandable component 104 is secured to the distal end 110 of the sleeve 102, for example, in an end to end or overlapping fashion. A variety of conventional techniques can be used for securing the distal end 146 of the elongate member 144 to the third portion 118 of the expandable component 104 including, for example, heat fusing, adhesive bonding, chemical bonding or mechanical attachment.

With continued reference to FIGS. 3A and 3B, in one embodiment, the elongate member 144 may be reciprocatably and axially moveable within the lumen 108 of the sleeve 102. For example, the elongate member 144 is axially moved distally until the expandable component 104 transitions from the collapsed configuration 120, illustrated in FIG. 3A, to a substantially-deployed configuration 130, illustrated in FIG. 3B. The expandable component 104 may be deployed into a shape suitable for capturing a medical implant by slideably moving the sleeve 102 distally relative to the expandable component 104.t. In a particular embodiment, the expandable component 104 is deployed into a conical shape. The expandable component 104 may be deployed beyond the distal end 110 of the sleeve 102 into a shape suitable for capturing a medical implant by axial movement of the elongate member 142 relative to the sleeve 102, or, alternatively, by relative sliding motion of the sleeve 102 relative to the expandable component 104.

Referring now to FIG. 4A, in another embodiment of the medical device 100 in accordance with the invention, the elongate member 144 has a lumen 150. In a further embodiment of the invention, the lumen 150 axially extends through the entire length of the elongate member 144. In a particular embodiment, illustrated in FIG. 4A, the lumen 122 of the expandable component 104 is continuous with the lumen 150 of the elongate member 144. The expandable component 104 may transition from the collapsed configuration 120, illustrated in FIG. 4A, to the fully-deployed configuration 126, illustrated in FIG. 4B, by axial movement of the elongate member 144 relative to the sleeve 102 beyond the distal end 110 of the sleeve 102, or alternatively, by relative sliding motion of the sleeve 102 relative to the expandable component 104. Referring to FIG. 4B, between the collapsed configuration 120 and the fully-deployed configuration 126, the expandable component 104 is deployed into substantially-deployed configuration 130 that includes a shape suitable for capturing a medical implant. In a particular embodiment, the expandable component 104 has a conical shape for capturing a medical implant. In a further embodiment, a guide wire may be inserted via the proximal end 148 of the elongate member 144 through the lumen 150 of the elongate member 144 and advanced through the lumen 122 of the expandable component 104 beyond the distal end 110 of the sleeve 102.

Figure 5A:
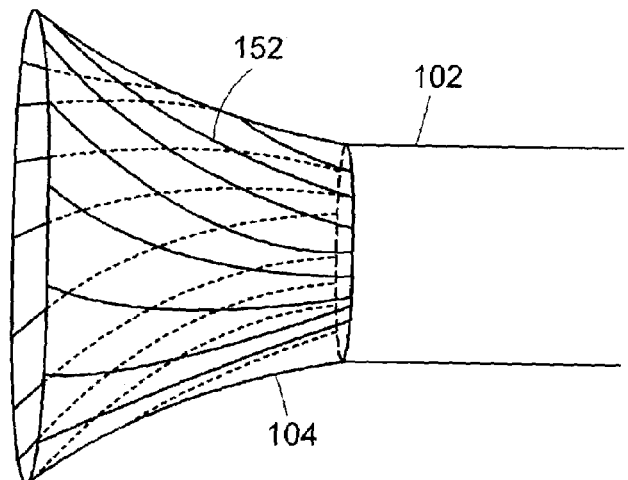
FIG. 5A illustrates a schematic side-view of an embodiment of the expandable component of a medical device in accordance with the invention in a deployed configuration.
Figure 5B:
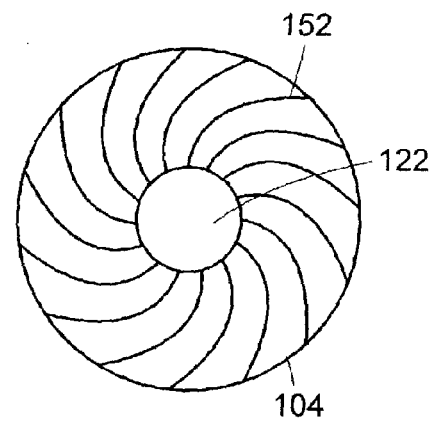
FIG. 5B illustrates a schematic end-view of the deployed configuration of an embodiment of the expandable component of the medical device illustrated in FIG. 5A.

Referring now to FIG. 5A, in the substantially-deployed configuration 130, the expandable component 104 is shaped and sized to accommodate the shape and size of the medical implant intended to be captured. In a particular embodiment, illustrated in FIG. 5A, the expandable component 104 is deployed into a conical shape. In yet another embodiment, referring now to FIG. 5B, the expandable component 104 has a generally circular cross-section.

Figure 5C:
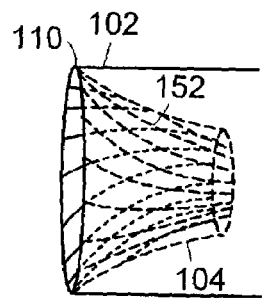
FIG. 5C illustrates a schematic side-view of an embodiment of the expandable component illustrated in FIG. 5A in a collapsed configuration.

Referring again to FIG. 5A, in one embodiment, the expandable component 104 includes flexible support arms 152 that provide increased rigidity to form the framework for the shape assumed by the expandable component 104 when at least a portion of the expandable component 104 is extruded beyond the distal end 110 of the sleeve 102. The arms 152 may be manufactured from a wire, such as spring wire. Referring now to FIG. 5C, the flexible support arms 152 occupy a reduced dimension in the radial direction when they are collapsed within the expandable component 104 in the collapsed configuration 120. Referring again to FIG. 5A, when the expandable component 104 is deployed beyond the distal end 110 of the sleeve 102, the flexible support arms 152 are released and spring outward to form the framework for the shape of the expandable component 104 in a deployed position.

The sleeve 102 is manufactured from biocompatible materials suitable for use inside a patient's body without causing damage to the vasculature. Suitable materials for the manufacture of the sleeve 102 include synthetic polymers such as polyethylene, polyurethane, polyglycolic acid, polyesters, polyamides, and mixtures, blends, copolymers thereof and any combinations of these materials. Preferred materials include polyesters such as polyfluorocarbons such as polytetrafluoroethylene (PTFE) with and without copolymerized hexafluoropropylene, and porous or nonporous polyurethanes. Especially preferred are the expanded fluorocarbon polymers.

Included in the class of preferred fluoropolymers are polytetrafluoroethylene (PTFE), fluorinated ethylene propylene (FEP), polyethylene terephthalate (PET), copolymers of tetrafluoroethylene (TFE) and perfluoro (propyl vinyl ether) (PFA), homopolymers of polychlorotrifluoroethylene (PCTFE), and its copolymers with TFE, ethylene-chlorotrifluoroethylene (ECTFE), copolymers of ethylene-tetrafluoroethylene (ETFE), polyvinylidene fluoride (PVDF), and polyvinyfluoride (PVF).

Figure 6:
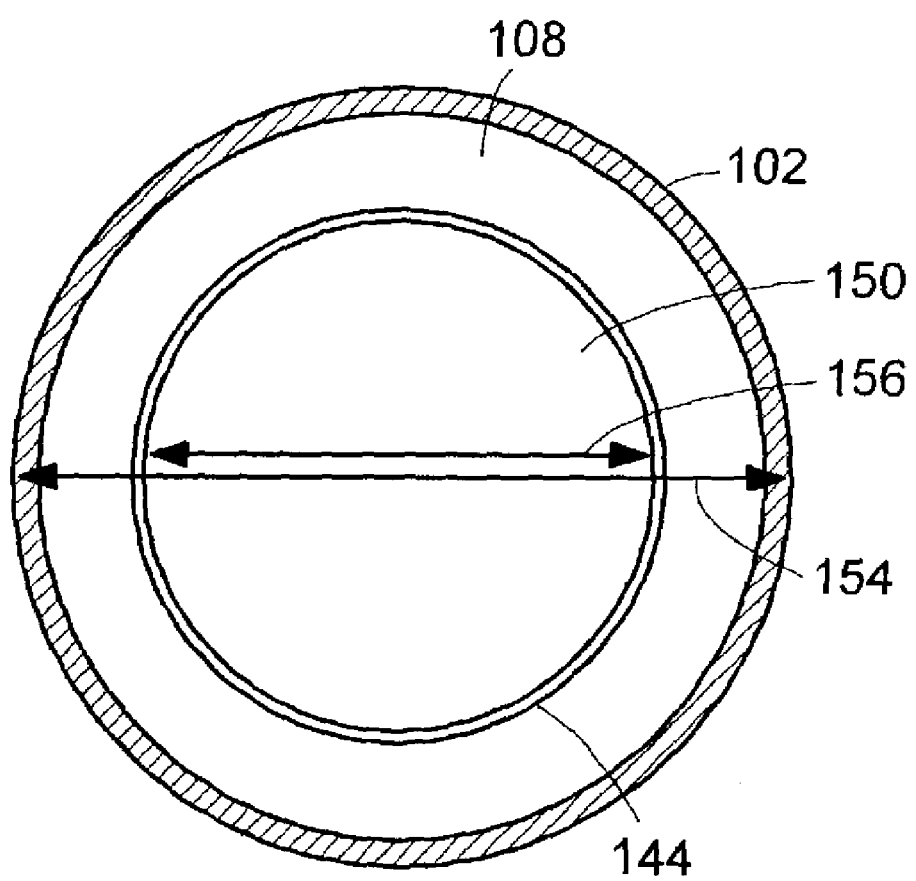
FIG. 6 is a cross-sectional view of the medical device of FIG. 4A through 6-6.

Referring to FIG. 6, the outer diameter 154 of the sleeve 102 and the inner diameter 156 of the lumen 150 of the elongate member 144 depend on the application inside a patient's body for which the medical device 100 is intended. For example, for capturing or delivering an intravascular distal protection filter, the outside diameter 154 of the sleeve 102 typically is in the range of about 0.4 mm to about 2.0 mm, preferably about 0.5 mm, and the inner diameter 156 of the elongate member 144 typically is in the range of about 0.2 mm to about 1.5 mm, preferably about 0.3 mm. Alternatively, for capturing or delivering a septal occluder, the outside diameter 154 of the sleeve 102 typically is in the range of 2 mm to about 6 mm, preferably about 5 mm, and the inner diameter 156 of the elongate member 144 typically is in the range of about 1.7 mm to about 5 mm, preferably about 4 mm.

The elongate member 144 can be made from a variety of materials and configurations. In one embodiment, the elongate member 144 is made from the same material as the sleeve 102. In another embodiment, the elongate member 144 and the sleeve 102 are manufactured from different materials. Suitable materials for the manufacture of the elongate member 144 include, for example, synthetic polymers such as polyethylene, polyurethane, polyglycolic acid, PEBAX (ATOFINA Chemicals, Inc., Philadelphia, Pa.), polyesters, polyamides, and mixtures, blends, copolymers thereof, and any combinations of these materials.

In one embodiment, the sleeve 102 may be coated with a radio-opaque material that enables a health care practitioner to track the medical device 100 of the invention by an imaging device while the medical device is used in a patient. In another embodiment, the flexible support arms 152 may be coated with a radio-opaque material, which enables a health care practitioner to visualize the expandable component 104 by an imaging device as the operator tracks and maneuvers the expandable component 104 between the collapsed configuration 120 and the deployed configurations during a medical procedure to capture or position a medical implant in a patient's body.

In another aspect, the invention is a method for manipulating, for example, for delivering or capturing a medical implant in the body of a patient using the medical device 100 according to the invention. For example, referring now to FIGS. 7A-7C, in one embodiment according to the invention, the medical device 100 includes a guide wire 158 for delivering or capturing a medical implant 160 in a patient's body. In a particular embodiment, the medical implant 160 is an intravascular distal protection filter that includes a central lumen 162 through which the guide wire 158 may be advanced.

Referring now to FIG. 7A, according to the method of the invention, a health care practitioner inserts the guide wire 158 into the medical device 100 via the proximal end 148 of the elongate member 144. The guide wire 158 is advanced proximally through the lumen 150 of the elongate member 144, the lumen 150 of the elongate member 144 being continuous with the lumen 122 of the expandable component 104.

Referring now to FIG. 7B, according to one embodiment of the invention, the guide wire 158 is advanced through the lumen 150 of the elongate member 144 into the lumen 122 of the expandable component 104. The medical device 100 is positioned relative to the medical implant 160 in the patient's body such that the lumen 162 of the medical implant 160 is aligned with the lumen 122 of the expandable component 104. With continued reference to 7B, in one embodiment, the guide wire 158 is advanced through the lumen 162 and beyond the distal portion of the medical implant 160.

The guide wire 158 may be used for positioning the medical implant 160 relative to the medical device 100 to capture the medical implant 160 with the medical device 100, as well as for removal of the medical implant 160 from the patient's body. For example, the expandable component 104 of the medical device 100 is moved from the collapsed position 120, illustrated in FIG. 7A, to the substantially-deployed position 130 illustrated in FIG. 7C, for subsequent capture of the medical implant 160. In a particular embodiment, illustrated in FIG. 7C, the expandable component 104 is deployed beyond the distal end 110 of the sleeve 102 to form a conical shape for capturing a medical implant. Referring to FIG. 7C, the expandable component 104 in the deployed position surrounds and captures the medical implant 160. The guide wire 158 is removed along with the medical device 100 from the patient's body, thereby retrieving the medical implant 160 from the patient's body.

Referring now to FIG. 8A, in another embodiment of the method of the invention, the medical device 100 may be used to insert or capture a medical implant having a guidewire 158 attached at its proximal end 166. Referring to FIG. 8B, the medical device 100 is positioned relative to the medical implant 160 such that the distal end 110 of the sleeve 102 is aligned with the free end 168 of the guide wire 158. In this embodiment, the guide wire 158 enters the medical device 100 at the distal end 110 of the sleeve 102 via the lumen 122 of the expandable component 104 which is continuous with the lumen 150 of the elongate member 144. Referring to FIG. 8C, the medical device 100 is advanced over the guide wire 158 or the guide wire 158 is advanced into the distal end 110 of the sleeve 102 of the medical device 100 until the medical device 100 is adjacent the medical implant 160. The elongate member 144 is distally moved to deploy the expandable component 104 into a substantially-deployed configuration 130 beyond the distal end 110 of the sleeve 102, for capturing the medical implant. The expandable component 104 may also be deployed by distally moving the sleeve relative to the expandable component.

Figure 9:
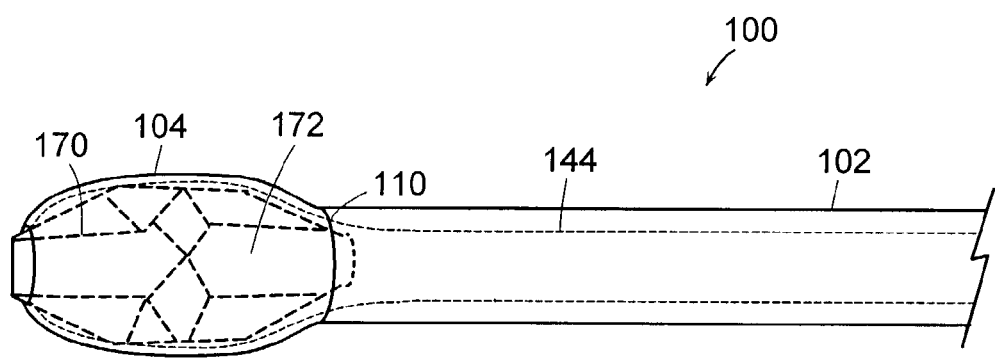
FIG. 9 illustrates a partially-sectioned schematic view of an embodiment of the medical device according to the invention including the expandable component in a substantially-deployed configuration covering the proximal pores of the distal protection filter.

Referring now to FIG. 9, in a particular embodiment according to the invention, the medical device 100 may be used to capture a distal protection filter 170 in a patient's body. A distal protection filter is a medical implant used for capturing embolic material that is dislodged during a medical procedure such as, angioplasty. While retrieving the distal protection filter 170, the expandable component 104 of the medical device 100 covers the pores 172 on the proximal portion 174 of the distal protection filter 170 thereby preventing the egress of embolic debris from the distal protection filter 170 during angioplasty.

Referring to FIGS. 10A-10C, in one embodiment according to the invention, the medical device 100 is used for capturing a collapsible medical implant 178 inside a patient's body. The medical device 100 is positioned relative to the collapsible medical implant 178, as illustrated in FIG. 10A, such that the distal end 110 of the sleeve 102 is aligned with the proximal end 180 of the collapsible implant 178. In one embodiment, the maximum diameter of the collapsible medical implant 178 in an uncollapsed state 182 is greater than the maximum diameter 154 of the lumen of the sleeve 102.

Referring to FIGS. 10B-10C, the sleeve 102 is slideably moved relative to the expandable element 104, deploying the expandable component 104 beyond the distal end 110 of the sleeve 102. As the expandable component 104 transitions between the collapsed configuration, illustrated in FIG. 10A, and the substantially-deployed configuration, illustrated in 10C, the extruded portion of the expandable component 104 radially compresses the medical implant 178, leading to collapse of the medical implant 178. The maximum diameter of the medical implant 178 decreases as the medical implant 178 transitions from the uncollapsed state 182 illustrated in FIG. 10A to the substantially-collapsed state 184, illustrated in FIG. 10C In all the foregoing aspects of the invention, a health practitioner can use a medical device 100 for the capture of medical implants used in the treatment of septal and atrial defects such as patent foramen ovale (PFO) and left atrial appendage (LAA).

In all the foregoing aspects of the invention, a health care practitioner can insert a medical device 100 of the invention inside a patient's body by a variety of means known in the art, including, for example, a catheter or a guide wire. In one method according to the invention, a health care practitioner inserts a medical device 100 of the invention via a catheter inside a patient's body. Following the insertion of the medical device 100 into the patient's body using a catheter, the expandable component 104 of the medical device 100 is deployed beyond the distal end of the catheter in the proximity of the medical implant to be captured inside the patient's body. The medical implant is captured by the expandable component 104 in the deployed configuration. Subsequent to the capture of the medical implant, both the medical device 100 and the captured medical implant are withdrawn into the larger bore diameter of the catheter for removal from the patient's body.

Other embodiments incorporating the concepts disclosed herein are within the spirit and scope of the invention. The described embodiments are illustrative of the invention and not restrictive.

What is claimed is:

1. A method for capturing a cardiovascular implant that has been implanted previously at an anatomical site in a patient's body comprising the steps of:

providing a medical device comprising a sleeve comprising a lumen, a distal end and a proximal end and an expandable component, wherein at least a portion of the expandable component is permanently joined to the distal end of the sleeve, the expandable component transitioning between a collapsed configuration wherein the expandable component is enclosed by the sleeve, and a deployed configuration wherein at least a portion of the expandable component that was enclosed by the sleeve while in the collapsed configuration expands to a size for capturing the cardiovascular implant upon extending beyond the distal end of the sleeve;

advancing the medical device to an anatomical site in a patient's body where the cardiovascular implant has been implanted previously; and transitioning the expandable component from the collapsed configuration to the deployed configuration such that at least a portion of the expandable component that was enclosed by the sleeve extends beyond the distal end of the sleeve while the expandable component remains permanently joined to the distal end of the sleeve, thereby surrounding and capturing with the expandable component the cardiovascular implant that has been implanted previously.

2. The method of claim 1, wherein the cardiovascular implant is a distal protection filter.

3. The method of claim 1, wherein the medical device further comprises an elongate member slideably moveable within the lumen of the sleeve.

4. The method of claim 1, wherein the expandable component is reciprocally moveable relative to the sleeve.

5. The method of claim 1, wherein the sleeve is reciprocally moveable relative to the expandable component.

6. The method of claim 1, wherein the cardiovascular implant is a septal occluder.

7. The method of claim 1, wherein the cardiovascular implant is a stent.

8. The method of claim 1, further comprising the step of removing the cardiovascular implant and the medical device from the patient.

9. The method of claim 1, where the expandable component is conical in shape.

* * * * *